United States Patent [19]

Irwin

[11] 4,269,965
[45] May 26, 1981

[54] AROMATIC POLYESTER WHICH FORMS OPTICALLY ANISOTROPIC MELTS AND FILAMENTS THEREOF

[75] Inventor: Robert S. Irwin, Wilmington, Del.

[73] Assignee: E. I. Du Pont de Nemours and Company, Wilmington, Del.

[21] Appl. No.: 76,799

[22] Filed: Sep. 17, 1979

[51] Int. Cl.$^3$ ............................................. C08G 63/60
[52] U.S. Cl. .................................. 528/128; 528/125; 528/191; 528/193; 528/220; 528/194
[58] Field of Search .............. 528/125, 128, 191, 193, 528/194, 220

[56] References Cited

U.S. PATENT DOCUMENTS

| | | | |
|---|---|---|---|
| 3,637,595 | 5/1969 | Cottis et al. | 528/193 |
| 4,066,620 | 1/1978 | Kleinschuster et al. | 528/193 |
| 4,067,852 | 1/1978 | Calundann | 528/193 |
| 4,083,829 | 4/1978 | Calundann et al. | 528/193 |
| 4,118,372 | 10/1978 | Schaefgen | 528/193 |
| 4,130,545 | 12/1978 | Calundann | 528/193 |

*Primary Examiner*—Lester L. Lee

[57] ABSTRACT

An aromatic polyester consisting essentially of (1) p-oxybenzoyl units or the 3-methyl- or 3-chloro-derivatives thereof; (2) 3,4'-dioxydiphenylether or 3,4'-dioxybenzophenone units or the 3'-methyl- or 3'-chloro-derivatives thereof or terephthaloyldi (3-methyl-4-oxybenzene) units; and (3) terephthaloyl units and filaments thereof.

16 Claims, No Drawings

AROMATIC POLYESTER WHICH FORMS OPTICALLY ANISOTROPIC MELTS AND FILAMENTS THEREOF

BACKGROUND OF THE INVENTION

1. Field of the Invention

This invention relates to fiber-forming melt-spinnable aromatic polyesters and to filaments thereof having high tenacity and high modulus.

2. Description of the Prior Art

A class of aromatic polyesters that form optically anisotropic melts from which oriented filaments can be melt spun has been described in Schaefgen U.S. Pat. No. 4,118,372. Most polyesters which are disclosed in this patent are derived primarily from para-oriented dihydric phenols and paraoriented dicarboxylic acids. Filaments that are melt-spun from such polyesters can be heat treated to high tenacity and modulus. Other polyesters are disclosed in the aforementioned Schaefgen patent which are copolymers derived from p-hydroxybenzoic acid, dihydric phenols and dicarboxylic acids.

Recent U.S. Pat. Nos. 4,067,852; 4,083,829; and 4,130,545 disclose polyesters consisting essentially of p-oxybenzoyl moieties, 2,6-dicarbonylnaphthalene moieties and various other moieties. U.S. Pat. No. 4,130,545 refers to an application Ser. No. 832,147 which claims an aromatic polyester consisting essentially of p-oxybenzoyl moiety, 2,6-dioxynaphthalene moiety and terephthaloyl moiety. The present invention does not employ a 2,6-dioxynaphthalene moiety. Applicant has found that the new polyesters may be melt spun into filaments which upon heat treatment exhibit high tenacity and high modulus.

SUMMARY OF THE INVENTION

The present invention is directed to fiber-forming copolyesters that exhibit optical anisotropy in the melt and consist essentially of units I, II, and III having the structural formulas:

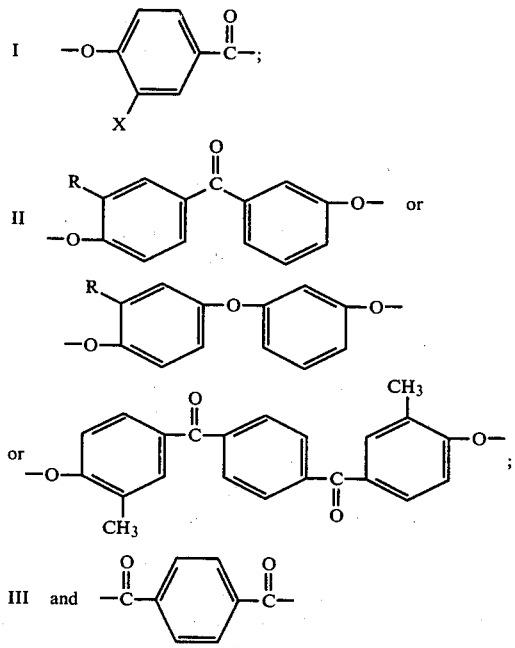

where X and R are independently hydrogen, methyl- or chloro-, in the proportions of about 50–75 mol % of Unit I, about 10–25 mol % of Unit II, and about 10–25 mol % of Unit III. From 0 to 10 mol % of

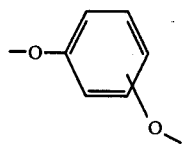

units selected from 1,3- or 1,4-dioxybenzene may also be present. Alternatively from 0 to 5 mol % of

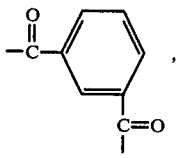

units may be present. Melt-spun and heat strengthened filaments of such polyesters are also contemplated.

DETAILED DESCRIPTION OF THE INVENTION

The copolyesters of the invention consist essentially of units as described above. Unit I is derived from p-hydroxybenzoic acid, or the 3-methyl or 3-chloro derivative thereof. Unit III is derived from terephthalic acid. Unit II is derived from 3,4'-dihydroxybenzophenone, 3'-methyl- or 3'-chloro-3,4'-dihydroxybenzophenone or 3,4'-dihydroxydiphenyl ether, 3'-methyl-, or 3'-chloro-3,4'-dihydroxydiphenylether or terephthaloyl di-(3-methyl-4-hydroxybenzene). The

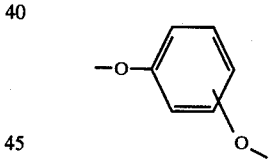

units are derived from resorcinol or hydroquinone and the

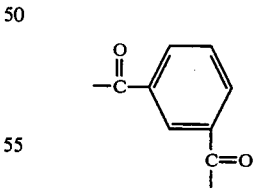

are derived from isophthalic acid. In place of such compounds one may usefully employ functional equivalents thereof as the reactants for preparing the copolyesters. The p-hydroxybenzoic acid reactant is preferably used in the form of its ester with a low-boiling aliphatic carboxylic acid.

The reactants are generally combined in proportions corresponding to the molar proportions of the units desired in the copolyester products. The p-hydroxybenzoic acid reactant or methyl- or chloroderivative thereof needed for 1,4-oxybenzoyl or the 3-methyl- or 3-chloro- derivative thereof (Unit I) should be reacted in an amount sufficient to supply from about 50 to 75 mol %, preferably about 60 mol %, of such units. When the upper or lower ends of the range are exceeded, there is a tendency towards polymer inhomogeneity. The reactants used to provide 3,4'-dioxydiphenylether or 3,4'-dioxybenzophenone or the 3'-methyl- or 3'-chloro-derivatives thereof or terephthaloyldi (3-methyl-4-oxybenzene) (Unit II) should be reacted in an amount sufficient to supply about 10 to 25 mol % of such units. A quantity of terephthalic acid reactant should be used to provide about 10 to 25 mol % of 1,4-dicarbonylphenylene (Unit III). The isophthalic acid reactant may be used to provide from 0–5 mol % of 1,3-dicarbonylphenylene units while the resorcinol or hydroquinone reactant may be employed in an amount sufficient to provide from 0–10 mol % of dioxyphenylene units. It will be apparent that in the polyester product there will be substantially equimolar quantities of units derived from diphenolic and dicarboxylic acid reactants respectively.

Conventional polymerization techniques may be employed such as described in the aforementioned U.S. Pat. No. 4,118,372 and more particularly in the examples described below. In general, a mixture of monomers (preferably with diacetates in up to 5% excess) is heated with stirring, under nitrogen, in a 250 ml 3-necked flask in a Wood's metal bath from approximately 250° C. to 330°–380° C. Polymerization is continued for up to a total of 0.5 to one hour until a fiber-forming molecular weight is reached but prior to excessive melt viscosity. Usually a vacuum, e.g., about 1.0 mm vacuum, is applied to obtain the final viscosity.

In single-stage polymerizations to produce the melt-spinnable polymers of this invention, the mole percentage of units derived from 4-hydroxybenzoic acid is limited to 70% and more practicably to about 65%. Above about 60%, particulate matter eventually forms during polymerization increasing in concentration with increasing mole percentage of 4-hydroxybenzoic acid (or its acetoxy derivative). Spinnability diminishes with increasing levels of particulate matter. While the mechanism for formation of particulate matter is not understood, it is believed to result from the tendency for 4-hydroxybenzoic acid (or its 3-methyl and 3-chloro derivatives) to form homo-oligomers in competition with random polymerization when its monomer concentration is too high. It is found that melt-spinnable polymers with at least 75 mol % of units from the aromatic hydroxyacid component are obtainable if the hydroxyacid component is added stepwise during polymerization. Preferably the original polymerization mixture contains only enough hydroxyacid component to provide 60 to 65 mol % of its units, polymerization is carried out to 80 to 90% conversion as indicated, for example, by the volume of acetic acid evolved, and then the remaining hydroxyacid component is added in one or more increments during continuation of polymerization to a viscosity required for melt-spinning.

The copolyesters of the invention exhibit optical anisotropy as determined by the thermooptical test (TOT) described in U.S. Pat. No. 4,118,372.

Filament Preparation

The (co)polyesters may be spun into filaments by conventional melt-spinning techniques. Filaments were prepared by melt-spinning into a quenching atmosphere of air or nitrogen and collected at a windup speed specified in the examples. With one exception the spinneret employed in the examples had a single capillary shaped as a right circular cylinder 0.23 mm in diameter and 0.46 mm long. The spinneret of Example IIC had 10 such identical capillaries. "Melt temperature" is the temperature at which the melt was maintained (values in parentheses are temperatures of the spinnerets).

As used herein, the term "as-spun" fiber refers to a fiber which has not been drawn or heat treated after extrusion and normal windup.

Heat Treatment and Utility

Following collection, samples of undrawn (as-spun) filament (or yarn in Example IIC) were heat-treated relaxed in an oven. Heating was in stages in a nitrogen atmosphere. Heating cycles are shown in abbreviated form as RT-100° C./2 hr+250° C./2 hr+280° C./18 hr which signifies that the sample was heated from room temperature (RT) to 200° C. in a 2-hour period, then heated at 250° C. for 2 hours, and finally heated at 280° C. for 18 hours.

The heat-treated fibers of this invention are useful for a variety of industrial applications such as plastic and rubber reinforcement.

Inherent viscosity ($\eta_{inh}$) was computed from $$\eta_{inh} = \ln(\eta_{rel})/C$$

where $\eta_{rel}$ is the relative viscosity and C is polymer concentration of 0.5 (i.e., 0.5 gm of polymer in 100 mL of solvent). Relative viscosity is the polymer solution to solvent ratio of flow times in a capillary viscometer at 25° C. The solvent employed was a mixture of 7.5% trifluoroacetic acid/17.5% methylene chloride/12.5% dichlorotetrafluoroacetone hydrate/12.5% perchloroethylene/50% 4-chlorophenol (all percentages by volume).

The polymers of this invention are anisotropic as determined using the thermooptical test (TOT) described in U.S. Pat. No. 4,118,372. Reported "flow temperatures" were obtained using this test. Alternatively (sometimes additionally) the polymers were characterized by "stick temperature" meaning the temperature of a thermal-gradient hot bar at the point at which the polymer first began to stick.

Filament tensile properties were measured using a recording stress-strain analyzer at 70° F. (21.1° C.) and 65% relative humidity. Sample lengths were 1.0 in (2.54 cm), and rate of elongation was 60%/min. Results are reported as D/T/E/M or T/E/M where D is linear filament density in tex units, T is break tenacity in dN/tex, E is elongation-at-break expressed as the percentage by which initial length increased, and M is initial tensile modulus in dN/tex. Since linear filament density is normally substantially unchanged by heat-treatment, it is reported only once.

Filaments of this invention have high heat-treated tenacities (e.g., about 10 dN/tex or greater) and high initial moduli (e.g., about 200 dN/tex or greater). Tensile properties reported in the examples are averages of several measurements (nearly always 5 or 6). There was sometimes considerable scatter among individual measurements. Thus, the maximum single tenacity value is also listed separately as the presumed best indication of property potential.

Synthesis of 3,4'-Diacetoxybenzophenone

This intermediate was prepared by either of two methods. In the first, a mixture of 100 g of m-anisic acid (0.658 mole), 250 g thionyl chloride (2.10 mole), and 5 mL of dimethylformamide was heated under reflux in a round-bottom flask with desiccant in the top of the condenser for exclusion of atmospheric moisture. Excess thionyl chloride was distilled from the product using a rotary film-evaporator at about 26.6 kPa pressure. The m-anisoyl chloride was then isolated by fractional distillation through a 25 cm Vigreux column at 109° C. and 1.6 kPa pressure.

A round-bottom flask fitted with a stirrer, dropping funnel, nitrogen inlet, and thermometer was cooled in an ice/water bath. The initial charge was a mixture of 69.0 g of anisole (0.638 mole), 90 g anhydrous aluminum trichloride (0.675 mole), and 108 mL tetrachloroethane. It was cooled to below 15° C. with stirring while a slow current of nitrogen passed over the mixture. A solution of 90 g of the above m-anisoyl chloride (0.528 mole) in 108 mL tetrachloroethane was added via the dropping funnel at a rate avoiding temperature increase of the stirred mixture to above 15° C. (addition period of 1 to 2 hr). Following mixing, the flask stood 2 days at room temperature before about 250 g of ice was carefully added to decompose the $AlCl_3$ complex. The tetrachloroethane was removed by steam distillation, and the organic products were separated from the aqueous mixture by extracting into 500 mL of methylene chloride followed by drawing off and discarding the aqueous layer. Two washes of the methylene chloride solution with about 200 mL of 5% aqueous sodium hydroxide and one wash with about 200 mL of water followed, removing and discarding the aqueous layer each time. After distilling off the methylene chloride using a rotary film-evaporator, 102 g of 3,4'-dimethoxybenzophenone (0.42 mole) remained which crystallized on cooling to room temperature. It was recrystallized from ethanol to yield 87 g.

Demethylation of the above product was accomplished by refluxing it for 15 hr in a mixture of 240 mL of 48% aqueous hydrobromic acid, 120 mL acetic acid, and 120 mL acetic anhydride. The dihydroxy product was isolated by pouring the cooled mixture into about 400 mL water, filtering, washing with water, and drying at 80° C.

The above product was acetylated by slurrying it (73 g; 0.34 mole) in 225 mL acetic anhydride. About 8 drops of concentrated sulfuric acid were added, and the mixture was heated 30 min on a steam bath. The resultant clear solution was cooled and then poured into about 600 mL of water to precipitate the product. It was filtered out, washed with water, and dried at about 80° C. Recrystallization from methanol yielded 80 g of 3,4'-diacetoxybenzophenone (0.268 mole) melting at 81°-83° C.

In the alternate procedure, 100 g m-hydroxybenzoic acid (0.724 mole) and 68.1 g phenol (0.724 mole) were mixed with 500 mL of hydrogen fluoride and the vessel was flushed with $BF_3$. The mixture was pressurized to 30 lb/in² gauge (207 kPa gauge) with $BF_3$ for 6 hr at 0° C. and then warmed to room temperature. A pink solid precipitated out on pouring the mixture into water. The precipitate was washed 5 times with water and then dried overnight under vacuum. The yield was 138 g of 3,4'-dihydroxybenzophenone melting at 195°-197° C. Acetylation was as described above.

Synthesis of 3'-chloro-3,4'-Diacetoxybenzophenone And 3'-Methyl-3,4'-Diacetoxybenzophenone These monomer materials were made using the alternate procedure described above for 3,4'-diacetoxybenzophenone except that (1) in place of phenol was used o-chlorophenol for preparing 3'-chloro-3,4'-diacetoxybenzophenone, and (2) in place of phenol was used o-methylphenol for preparing 3'-methyl-3,4'-diacetoxybenzophenone.

Synthesis of 3,4'-Diacetoxydiphenyl Ether

Into a 1-liter flask equipped with a stirrer, nitrogen inlet, and Vigreux column with a distillation head were charged 200 g m-methoxyphenol (50% excess)
200 g p-bromoanisole
60 g sodium hydroxide
6 g copper powder.

The mixture was heated, with stirring under nitrogen, at 240° C. until all the water had evolved and then for 5 more hours. After cooling, it was poured into a solution of 60 g KOH in 1100 mL of water. After thorough shaking with ether, the water layer was discarded. The ether solution was washed by shaking with water and then dried by evaporation. The residue was distilled at 160° C./1.6 mm Hg (0.21 kPa) to yield 126 g of crude 3,4'-dimethoxydiphenyl ether. The product was refluxed overnight in a medium composed of 315 mL of 48% hydrobromic acid, 160 mL of acetic anhydride, and 160 mL of acetic acid. It was poured into 1 liter of water, extracted with ether, and evaporated to yield 91 g of deep red-brown product melting at 105°-112° C. It was recrystallized from chloroform containing a very small amount of ethyl alcohol. Color was unchanged. Yield was 72 g melting at 113°-118° C. Acetylation was by heating the product, along with about 216 mL acetic anhydride and a few drops of conc. sulfuric acid, on a steam bath for 1.5 hr. On pouring the mixture into cold water, an off-white solid precipitated out which was recrystallized from ethyl alcohol to yield 108 g of 3,4'-diacetoxydiphenylether melting at 89°-92° C.

Synthesis of Terephthaloyldi (3-Methyl-4-Hydroxybezene) and its Diacetate, Terephthaloyldi (3-Methyl-4-acetoxybenzene) (TDMP)

The following reaction shows the major part of this synthesis.

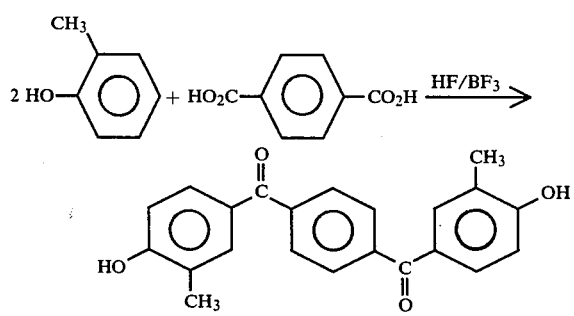

A 1 L autoclave was charged with 49.8 g (0.3 mole) of terephthalic acid, 69.1 g (0.64 mole) of o-cresol, and 500 mL of hydrofluoric acid (cooled to 0° C.). The autoclave was closed, attached to a cylinder of $BF_3$, and kept at 0° C. for 6 hours with agitation while under a BF$_3$ pressure of 30 psi (207 kPa). The crimson red product was isolated by precipitation in approximately 2 L of water, filtration, further water washing, and drying at about 100° C. in an air oven. Yield was 103 g (100%) of a crude product melting at about 352° C. The crude diol was acetylated by refluxing 3 hr in about 300 mL of acetic anhydride containing about 0.25 g of sulfuric acid. The diacetate was isolated as for the diol, yielding 121 g (94%) of a product melting at 200°–208° C. After recrystallization from a 70/30 mixture of chloroform and ethanol, the diacetate was a white solid melting at 207°–211° C.

EXAMPLES

The same general procedure was used in all the examples.

The monomer ingredients were added to a 3-necked flask in substantially the same molar ratios as desired in the final polymer except that an excess (usually 3 or 5%) of diacetates was often used. The resultant polymer is identified, for example, as

HBA/DPE/TPA (60/20/20)

meaning it was prepared from 60 mol % 4-acetoxybenzoic acid, 20 mole % 3,4'-diacetoxydiphenylether, and 20 mol % terephthalic acid (excesses of diacetates are not included in these percentages).

The 3-necked flask was fitted with: (1) a glass stirrer extending through a pressure-tight resin bushing, (2) a nitrogen inlet, and (3) a short Vigreux column leading to a water-cooled condenser with a flask for collecting acetic acid by-product. Provision for applying vacuum was in the adapter for the Vigreux column. An electrically heated Wood's metal bath mounted for vertical adjustment was used for heating. The reaction mixture was heated to increasing temperatures with stirring at atmospheric pressure under nitrogen purge until essentially all the acetic acid had evolved. Then, under a vacuum of usually about 0.027 kPa, heating was continued until viscosity had increased to a level believed satisfactory for melt-spinning. The cooled and solidified polymer was comminuted, and a portion was molded into a cylindrical plug for spinning.

EXAMPLE I

Filaments from Polymers of 4-Acetoxybenzoic Acid (HBA), 3,4'-Diacetoxybenzophenone (DHB), Terephthalic Acid (TPA), and Alternatively Either Resorcinol Diacetate (RE) or Isophthalic Acid (IPA).

Polymerization Ingredients

| Run | HBA | DHB | TPA | RE or IPA | Mole Ratios HBA/DHB/TPA/RE or IPA |
|---|---|---|---|---|---|
| A | 27.0 | 14.9 (0%) | 8.3 | — | 60/20/20 |
| B | 21.6 | 12.28 (3%) | 4.98 | 1.66 IPA | 60/20/15/5 |
| C | 64.8 | 17.88 (0%) | 19.9 | 11.64(0%)RE | 60/10/20/10 |
| D | 10.8 | 9.38 (5%) | 4.98 | — | 50/25/25 |

Polymerization Temperatures

| Run | Atmospheric Pressure | | Vacuum |
|---|---|---|---|
| A | 240–376° C./395 min. | | — |
| B | 282–340° C./23 min. | + | 340–346/5 min. |
| C | 228–328° C./346 min. | + | 328–331/8 min. |
| D | 288–350° C./39 min. | + | 350–360° C./4 min. |

Polymer Characterizations

| Run | Inherent Viscosity | Flow Temp. (°C.) | Stick Temp. (°C.) |
|---|---|---|---|
| A | 1.69 | 291 | 293 |
| B | 0.97 | — | 320 |
| C | 1.16 | 267 | 250 |
| D | 1.24 | — | 285 |

Filament Extrusion

| Run | Melt Temp. (°C.) Cell (Spinneret) | Windup Speed (m/min) |
|---|---|---|
| A | 396 (394) | 549 |
| B | 335 (337) | 549 |
| C | 279 (284) | 457 |
| D | 340 (345) | 549 |

Heat Treatment

| Run | Cycle |
|---|---|
| A | 230° C./2 hr + 250° C./2 hr + 280° C./2 hr + 305° C./18 hr |
| B | 220° C./2 hr + 250° C./2 hr + 270° C./2 hr + 280° C./18 hr |
| C-1 (yarn) | 225° C./20 hr |
| C-2 (yarn) | 225° C./20 hr + 250° C./3 hr + 275° C./20 hr |
| D | 220° C./2 hr + 240° C./2 hr + 260° C./2 hr + 280° C./1 hr + 290° C./18 hr |

Tensile Properties

| Run | As-Spun D/T/E/M | Heat Treated T/E/M | Max. T |
|---|---|---|---|
| A | 0.66/3.0/1.0/297 | 12.2/2.3/493 | 15.4 |
| B | 0.71/3.2/0.9/379 | 14.6/3.1/479 | 16.6 |

| | -continued | | |
|---|---|---|---|
| C-1 (fil) | 0.65/3.0/1.3/245 | 6.8/2.5/240 | 12.5 |
| C-2 (yarn) | 0.65/3.0/1.3/245 | 15.8/6.8/256 | 16.3 |
| D | 0.89/3.3/0.9/368 | 6.4/1.6/423 | 10.6 |

Runs C-1 and C-2, representing two different heat treatments of the same as-spun yarn, show that the heat-treating temperature did affect the level of attained tenacity. In fact, tensile properties of all products of the invention are very dependent on the maximum heat-treating temperature employed, and many of the tenacities reported could have been improved considerably by careful optimization of heat-treatment temperatures.

The relatively low tenacity shown for Run D indicates that the minimum useful level of units from 4-hydroxybenzoic acid is about 50 mol %.

EXAMPLE II

Filaments from Polymers of 4-Acetoxybenzoic Acid (HBA) 3'-Methyl-3,4'-Diacetoxybenzophenone (MDHB) or 3'-Chloro-3,4'-Diacetoxybenzophenone (CDHB) and Terephthalic Acid (TPA) and Optionally with Resorcinal Diacetate (RE)

Polymerization Ingredients

| | | Grams Used | | | Mole Ratios CDHB |
|---|---|---|---|---|---|
| Run | HBA | CDHB or MDHB | TPA | RE | HBA/MDHB/TPA/RE |
| A | 21.60 | M-12.98(4%) | 6.64 | — | 60/20/20 |
| B | 21.60 | M-9.73(4%) | 6.64 | 2.02(4%) | 60/15/20/5 |
| C | 10.8 | C-6.98(5%) | 3.32 | — | 60/20/20 |

Polymerization Temperatures

| Run | Atmospheric Pressure | | Vacuum |
|---|---|---|---|
| A | 280–322° C./27 min. | + | 322–330° C./10 min. |
| B | 280–330° C./23 min. | + | 330–335° C./5 min. |
| C | 260–356° C./43 min. | + | 356° C./1 min. |

Polymer Characterizations

| Run | Inherent Viscosity | Stick Temp. (°C.) |
|---|---|---|
| A | 1.04 | 255 |
| B | 0.73 | 240 |
| C | 1.21 | 280 |

Filament Extrusion

| Run | Melt Temp. (°C.) Cell (Spinneret) | Windup Speed (m/min) |
|---|---|---|
| A | 325 (330) | 549 |
| B | 290 (298) | 549 |
| C | 334 (340) | 549 |

Heat Treatment

| Run | Cycle |
|---|---|
| A | RT-200° C./2 hr + 200–304° C./7 hr + 304° C./7 hr |
| B | RT-200° C./2 hr + 200–304° C./7 hr + 304° C./7 hr |
| C | RT-200° C./2 hr + 200–304° C./7 hr + 304° C./7 hr |

Tensile Properties

| Run | As-Spun D/T/E/M | Heat Treated T/E/M | Max. T |
|---|---|---|---|
| A | 0.66/2.9/0.7/400 | 15.5/3.0/522 | 19.1 |
| B | 0.63/2.4/0.7/342 | 11.0/2.6/451 | 15.8 |
| C | 0.78/3.3/0.9/361 | 8.8/1.9/469 | 16.9 |

Improved properties and property uniformity may be expected from optimization of heat-treating conditions.

EXAMPLE III

Filaments from Polymers of 3-Chloro-4-Acetoxybenzoic Acid (CHBA), 3,4'-Diacetoxybenzophenone (DHB), and Terephthalic Acid (TPA) and Alternatively Either Resorcinol Diacetate (RE) or Isophthalic Acid (IPA)

Polymerization Ingredients

| | | Grams Used | | | Mole Ratios |
|---|---|---|---|---|---|
| Run | CHBA | DHB | TPA | RE or IPA | CHBA/DHB/TPA/RE or IPA |
| A | 12.88 | 6.2 (4%) | 3.32 | — | 60/20/20 |

-continued

| | | | | | |
|---|---|---|---|---|---|
| B | 12.88 | 6.2 (4%) | 3.32 | — | 60/20/20 |
| C | 12.87 | 4.68(5%) | 3.3 | 1.0(5%)RE | 60/15/20/5 |
| D | 19.32 | 4.62(3%) | 4.98 | 3.10(7%)RE | 60/10/20/10 |
| E | 12.87 | 6.26(5%) | 2.5 | 0.83 IPA | 60/20/15/5 |

Polymerization Temperatures

| Run | Atmospheric Pressure | | Vacuum |
|---|---|---|---|
| A | 270–385° C./69 min. | + | 385° C./5–10 min. |
| B | 270–368° C./25 min. | + | 368–370/1 min. |
| C | 272–376° C./23 min. | + | 376° C./3 min. |
| D | 276–300° C./48 min. | + | 300° C./5 min. |
| E | 262–366° C./24 min. | + | 366° C./3 min. |

Polymer Characterizations

| Run | Inherent Viscosity | Stick Temp. (°C.) |
|---|---|---|
| A | 1.59 | 330 |
| B | 0.99 | 260 |
| C | Insol. | 280 |
| D | Insol. | 318 |
| E | 0.78 | 266 |

Filament Extrusion

| Run | Melt Temp. (°C.) Cell (Spinneret) | Windup Speed (m/min) |
|---|---|---|
| A | 371 (385) | 137 |
| B | 325 (330) | 549 |
| C | 342 (342) | 549 |
| D | 382 (382) | 137 |
| E | 335 (345) | 549 |

Heat Treatment

| Run | Cycle |
|---|---|
| A | 230° C./2 hr + 250° C./2 hr + 280° C./2 hr + 320° C./12 hr |
| B | RT-200° C./2 hr + 200–304° C./7 hr + 304° C./7 hr |
| C | 230° C./2 hr + 250° C./2 hr + 270° C./2 hr + 290° C./20 hr |
| D | RT-200° C./2 hr + 200–304° C./7 hr + 304° C./7 hr |
| E | 280° C./16 hr |

Tensile Properties

| Run | As-Spun D/T/E/M | Heat Treated T/E/M | Max. T |
|---|---|---|---|
| A | 3.2/5.4/2.0/301 | 8.4/2.9/324 | 9.2 |
| B | 0.55/2.9/0.8/343 | 19.8/4.4/441 | 22.1 |
| C | 0.68/3.4/0.8/371 | 16.2/3.4/530 | 18.5 |
| D | 2.27/5.4/2.0/338 | 5.7/4.0/183 | 14.0 |
| E | 0.59/4.3/1.3/385 | 8.5/3.0/343 | 10.2 |

EXAMPLE IV

Filaments from Polymers of 3-Methyl-4-Acetoxybenzoic Acid (MHBA), 3,4'-Diacetoxybenzophenone (DHB), Terephthalic Acid (TPA) and Alternatively Either Resorcinol Diacetate (RE) or Isophthalic Acid (IPA)

Polymerization Ingredients

| | Grams Used | | | | Mole Ratios |
|---|---|---|---|---|---|
| Run | MHBA | DHB | TPA | RE or IPA | MHBA/DHB/TPA/RE or IPA |
| A | 7.76 | 4.08 (5%) | 2.16 | — | 60/20/20 |
| B | 11.64 | 4.68 (5%) | 3.32 | 1.02(5%)RE | 60/15/20/5 |
| C | 7.76 | 3.88 (0%) | 1.66 | 0.55 IPA | 60/20/15/5 |
| D | 13.58 | 4.68 (5%) | 1.66 | 0.83 IPA | 70/15/10/5 |

Polymerization Temperatures

| Run | Atmospheric Pressure | | Vacuum |
|---|---|---|---|
| A | 270–344° C./20 min. | + | 344–360° C./9 min. |
| B | 260–350° C./18 min. | + | 350–360° C./7 min. |
| C | 262–340° C./20 min. | + | 340–350° C./5 min. |
| D | 260–368° C./36 min. | + | 368° C./3 min. |

-continued

Polymer Characterizations

| Run | Inherent Viscosity | Stick Temp. (°C.) |
|---|---|---|
| A | Insol. | 284 |
| B | 1.11 | 246 |
| C | Insol. | 240 |
| D | Insol. | 250 |

Filament Extrusion

| Run | Melt Temp. (°C.) Cell (Spinneret) | Windup Speed (m/min) |
|---|---|---|
| A | 330 (330) | 549 |
| B | 320 (322) | 549 |
| C | 320 (320) | 411 |
| D | 375 (378) | 274 |

Heat Treatment

| Run | Cycle |
|---|---|
| A-1 | RT-200° C./2 hr + 200–304° C./7 hr + 304° C./7 hr |
| A-2 | 230° C./2 hr + 250° C./2 hr + 270° C./2 hr + 290° C./12 hr |
| B-1 | RT-200° C./2 hr + 200–304° C./7 hr + 304° C./7 hr |
| B-2 | 230° C./2 hr + 250° C./2 hr + 270° C./2 hr + 290° C./10 hr |
| C-1 | RT-200° C./2 hr + 200–304° C./7 hr + 304° C./7 hr |
| C-2 | 280° C./16 hr |
| D | RT-200° C./2 hr + 200–304° C./7 hr + 304° C./7 hr |

Tensile Properties

| Run | As-Spun D/T/E/M | Heat Treated T/E/M | Max. T |
|---|---|---|---|
| A-1 | 0.82/5.2/1.1/503 | 7.3/2.0/393 | 10.4 |
| A-2 | 0.82/5.2/1.1/503 | 10.3/2.8/389 | 14.7 |
| B-1 | 0.62/4.5/1.4/366 | 9.4/3.9/283 | 13.6 |
| B-2 | (same) | 12.9/3.2/441 | 18.3 |
| C-1 | 0.94/4.9/1.5/392 | 4.5/2.5/207 | 5.9 |
| C-2 | (same) | 7.8/3.4/299 | 9.7 |
| D | 1.24/2.8/0.9/299 | 5.3/2.7/247 | 6.2 |

The two sets of heat-treated tensile properties for Runs B and C again illustrate the importance of choosing the proper maximum heat-treating temperature. It was too high for Runs B-1 and C-1. Run B shows that addition of resorcinol diacetate can increase both tenacity and initial modulus. Run C indicates that no more than about 5 mol % isophthalic acid is effective in this system. And Run D indicates that 70 mol % is too much 3-methyl-4-hydroxybenzoic acid for obtaining good properties.

EXAMPLE V

Filaments from Polymers of
3-Methyl-4-Acetoxybenzoic Acid (MHBA),
3′-Methyl-3,4′-Diacetoxybenzophenone (MDHB) and
Terephthalic Acid (TPA)

Polymerization Ingredients 11.64 g of 3-methyl-4-acetoxybenozic acid,
6.55(5%) g of 3′-methyl-3,4′-diacetoxybenzophenone, and
3.32 g of terephthalic acid to yield MHBA/MDHB/TPA (60/20/20) were polymerized by heating from 260° to 350° C. in 34 min at atmospheric pressure and then from 350° to 348° C. in 2 min under vacuum. The inherent viscosity was 0.93, and the polymer exhibited a stick temperature of 256° C. A single filament was spun from the melt at 334° C. with a windup speed of 549 m/min. Heat-treatment of the collected filament was at RT-200° C./2 hr+200°–304° C./7 hr+304° C./7 hr. The tensile properties were:

| As-Spun D/T/E/M | Heat Treated T/E/M | Max. T |
|---|---|---|
| 0.68/2.8/0.8/373 | 10.7/2.4/477 | 12.6 |

EXAMPLE VI

Filaments from Polymers of 4-Acetoxybenzoic Acid (HBA), 3,4′-Diacetoxydiphenylether (DPE), Terephthalic Acid (TPA), and Alternatively Either Resorcinol Diacetate (RE) or Isophthalic Acid (IPA)

Polymerization Ingredients

| | Grams Used | | | | Mole Ratios |
|---|---|---|---|---|---|
| Run | HBA | DPE | TPA | RE or IPA | HBA/DPE/TPA/RE or IPA |
| A | 27.0 | 15.02(5%)* | 8.3 | — | 60/20/20 |
| B | 21.6 | 11.78(3%) | 6.64 | — | 60/20/20 |
| C | 28.8 | 11.05(3%) | 7.47 | 1.50(3%)RE | 64/15/18/3 |
| D | 27.0 | 11.05(3%) | 8.30 | 2.50(3%)RE | 60/15/20/5 |

-continued

| E | 27.0 | 14.73(3%) | 6.23 | 2.08 IPA | 60/20/15/5 |

*( ) indicates % excess of diacetates.

Polymerization Temperatures

| Run | Atmospheric Pressure | | Vacuum |
|---|---|---|---|
| A | 256–344° C./53 min. | + | 344–350/7 min. |
| B | 268–340° C./42 min. | + | 340–348/7 min. |
| C | 268–348° C./55 min. | + | 348/16 min. |
| D | 270–340° C./54 min. | + | 340–343° C./7 min. |
| E | 272–350° C./65 min. | | |

Polymer Characterizations

| Run | Inherent Viscosity | Stick Temp. (°C.) |
|---|---|---|
| A | 1.39 | 265 |
| B | 1.24 | 255 |
| C | 1.50 | 270 |
| D | 1.37 | 235 |
| E | 1.19 | 234 |

Filament Extrusion

| Run | Melt Temp. (°C.) Cell (Spinneret) | Windup Speed (m/min) |
|---|---|---|
| A | 329 (333) | 549 |
| B | 328 (330) | 549 |
| C | 332 (336) | 549 |
| D | 292 (296) | 549 |
| E | 352 (353) | 549 |

Heat Treatment

| Run | Cycle |
|---|---|
| A | 230° C./2 hr + 250° C./2 hr + 280° C./18 hr |
| B | RT-200 ° C./2 hr + 200–305° C./7 hr + 305° C./7 hr |
| C | 230° C./2 hr + 250° C./2 hr + 280° C./20 hr |
| D | 230° C./2 hr + 250° C./2 hr + 270° C./2 hr + 280° C./18 hr |
| E | 230° C./2 hr + 260° C./2 hr + 280° C./20 hr |

Tensile Properties

| Run | As-Spun D/T/E/M | Heat Treated T/E/M | Max. T |
|---|---|---|---|
| A | 0.59/2.5/0.78/317 | 13.1/2.8/434 | 16.1 |
| B | 0.64/2.0/0.68/266 | 14.3/3.2/406 | 17.2 |
| C | 0.65/0.3/0.43/67 | 13.6/3.5/360 | 15.7 |
| D | 0.63/3.0/0.88/352 | 11.6/2.8/411 | 13.8 |
| E | 0.65/2.9/1.21/222 | 11.0/3.1/360 | 11.5 |

Runs A and B, without any added m-phenylene units, were essentially identical except that, for Run B, a higher maximum heat-treatment temperature was employed. As revealed in the tabulation of Tensile Properties, a slightly increased tenacity was obtained in Run B. Very high initial moduli and excellent tenacities were obtained in both runs.

Runs C and D employed additionally units from resorcinol (i.e., m-phenylene chain units) at modified mole ratios of units. Again, very high initial moduli and excellent tenacities resulted.

Run E used m-phenylene units from isophthalic acid rather than from resorcinol as in Run D, but was otherwise substantially equivalent to Run D. Excellent tensile properties resulted.

EXAMPLE VII

Filaments From Polymers of 4-Acetoxybenzoic Acid (HBA), 3′-Methyl-3,4′-Diacetoxybenzophenone (MDHB), Terephthalic Acid (TPA), and Resorcinol Diacetate (RE)

This example describes two-stage addition (Run A) and a control one-stage addition (Run B) of HBA to provide 70 mol % of units from HBA in the polymer prepared.

Initial Polymerization Ingredients

| | Grams Used | | | | Mole Ratios |
|---|---|---|---|---|---|
| Run | HBA | MDHB | TPA | RE | HBA/MDHB/TPA/RE |
| A | 10.8 | 4.34 (5%) | 3.32 | 1.36 (5%) | |
| B | 12.6 | 3.28 (5%) | 2.49 | 1.02 (5%) | 70/10/15/5 |

Initial Polymerization

| Run | Atmospheric Pressure | | Vacuum |
|---|---|---|---|
| A | 270–340° C./30 min. | | |
| B | 270–340° C./30 min. | + | 340° C./2 min. |

At this point, polymer preparation for the control (Run B) was complete. For Run A, however, an additional 6.0 g of HBA was added all at once with continuation of polymerization.

Continued Polymerization

| Run | Atmospheric Pressure | | Vacuum |
|---|---|---|---|
| A | 340–356° C./13 min. | + | 356° C./1 min. |

Final mole ratio for Run A was the same as for Run B at HBA/MDHB/TPA/RE=70/10/15/5.

Polymer Characterizations

| Run | [η] | Stick Temp. (°C.) |
|---|---|---|
| A | 1.31 | 260 |
| B | 1.13 | 280 |

Filament Extrusion

| Run | Melt Temp. (°C.) Cell (Spinneret) | Winding Speed (m/min) | No. of Holes |
|---|---|---|---|
| A | 332 (340) | 549 | 1 |
| B | 336 (340) | 549 | 1 |

Heat Treatment

| Run | Cycle |
|---|---|
| A-1 | RT-200° C./2 hr + 200-304° C./7 hr + 304° C./7 hr |
| A-2 | RT-230° C./2 hr + 250° C./2 hr + 270° C./2 hr + 290° C./10 hr |
| B-1 | RT-200° C./2 hr + 200-304° C./7 hr + 304° C./7 hr |
| B-2 | RT-230° C./2 hr + 250° C./2 hr + 270° C./2 hr + 290° C./10 hr |

Tensile Properties

| Run | As-Spun D/T/E/M | Heat Treated T/E/M | Maximum T |
|---|---|---|---|
| A-1 | 0.60/2.9/0.7/420 | 8.8/2.2/402 | 9.9 |
| A-2 | (same) | 10.8/2.1/443 | 11.8 |
| B-1 | (not measured) | 8.7/2.6/417 | 10.1 |
| B-2 | (same) | 8.6/2.3/411 | 10.4 |

While not apparent from the above results, polymer melt in Run A was clear and the melt-spun filaments were lustrous. For Run B, however, the filaments were somewhat less lustrous indicating the presence of particulate material.

EXAMPLE VIII

Filament From A Polymer of
3-Methyl-4-Acetoxybenzoic Acid (MHBA),
3,4′-Diacetoxybenzophenone (DHB), Terephthalic
Acid (TPA), and Resorcinol Diacetate (RE)

A mixture of 11.64 g MHBA (0.06 mole), 4.14 g of DHB (0.0139 mole, 5% excess), 3.32 g TPA (0.02 mole) and 1.35 g RE (0.007 mole, 5% excess) was heated from 270° C. to 350° C. during 30 min. After drawing a vacuum for 30 sec., another 6.40 g of MHBA (0.033 mole) was added, vacuum was reapplied, and heating continued 2 more minutes to 360° C. Inherent viscosity was 1.04, and the stick temperature was 270° C. A single filament was press-spun through a 0.23 mm diameter orifice at a melt temperature of 331° C. (spinneret temperature of 336° C.) and wound up at 549 m/min. Mole ratios for the polymer were 70/10/15/5 (MHBA/DHB/TPA/RE).

Averaged tensile properties for the as-spun filament were:
tex/filament=0.69
tenacity (dN/tex)=2.8
elongation (%)=0.9
modulus (dN/tex)=324

Portions of the filament were heat-treated in two different cycles.

Cycle 1: RT-230° C./2 hr+250° C./2 hr+270° C./2 hr+290° C./10 hr

Average Tensile Properties tenacity (dN/tex)=7.9 (max.=9.25)
elongation (%)=2.4
modulus (dN/tex)=345

Cycle 2: RT-200° C./2 hr+200°-304° C./7 hr+304° C./7 hr

Average Tensile Properties tenacity (dN/tex)=6.3 (max.=7.42)
elongation (%)=2.2
modulus (dN/tex)=304

The filament was of excellent luster.

EXAMPLE IX

Filament From A Polymer of 4-Acetoxybenzoic Acid
(HBA), 3′-Methyl-3,4′-Diacetoxybenzophenone
(MDHB), Terephthalic Acid (TPA), and Resorcinol
Diacetate (RE)

A mixture of 10.8 g (0.060 mole) of HBA, 3.28 g (0.0105 mole, 5% excess) of MDHB, 2.75 g (0.0166 mole) of TPA, and 1.35 g (0.00698 mole, 5% excess) of RE was heated from 250° C. to 358° C. in 22 min. After drawing a vacuum for 1 min, another 7.0 g (0.0389 mole) of HBA was added. Heating continued 5 more minutes to 380° C. when vacuum was reapplied for 30 sec. The stick temperature was 270° C., and the product was incompletely soluble in the solvent for inherent viscosity measurement. A single filament was press-spun through a 0.23 mm diameter orifice at a melt temperature of 365° C. (spinneret temperature 378° C.) and wound at 549 m/min. Mole ratios for the polymer were:
75/7.5/12.5/5(HBA/MDHB/TPA/RE)

Tensile properties for the as-spun filament were not measured. After heat-treatment at RT-200° C./2 hr+200°-304° C./7 hr+304° C./7 hr the average tensile properties were:
tex/filament=0.75
tenacity (dN/tex)=9.5 (max.=10.5)
elongation (%)=2.1
modulus (dN/tex)=397

Particulate matter was present in the melt, and spinning performance was marginal. It was, however, possible to collect fiber of very good properties from a polymer comprising 75 mol % of hydroxyacid units.

EXAMPLE X

Filament From A Polymer of 4-Acetoxybenzoic Acid
(HBA), Terephthaloyldi (3-Methyl-4-Acetoxybenzene)
(TDMP), And Terephthalic Acid (TPA)

A mixture of 16.2 g HBA (0.090 mole), 13.1 g TDMP (0.0306 mole, 2% excess), and 4.98 g TPA (0.030 mole) was heated at atmospheric pressure from 282° C. to 334° C. during 28 min and then under a vacuum of 2 mm Hg (0.267 kPa) from 334° C. to 350° C. during 6 min. Mole ratios for the resultant polymer were:

60/20/20(HBA/TDMP/TPA)

Inherent viscosity was 1.14, and the stick temperature was 210° C.

The polymer was press-spun through a single orifice of 0.23 mm diameter and wound at 549 m/min. Averaged properties for the as-spun filament were:
tex/filament=1.01
tenacity (dN/tex)=4.29
elongation (%)=2.0
modulus (dN/tex)=277
Heat treatment of the as-spun fiber was according to the cycle RT-200° C./2 hr+200°-304° C./7 hr+304° C./7 hr Averaged properties for the heat-treated filament were:

tenacity (dN/tex)=8.33 (max.=10.7)
elongation (%)=3.65
modulus (dN/tex)=243

EXAMPLE XI

Filaments From Polymers of 4-Acetoxybenzoic Acid (HBA), Terephthaloyldi (3-Methyl-4-Acetoxybenzene) (TDMP), Terephthalic Acid (TPA), and Hydroquinone Diacetate (HQ)

Polymerization Ingredients

| | Grams Used | | | | Mole Ratios |
|---|---|---|---|---|---|
| Run | HBA | TDMP | TPA | HQ | HBA/TDMP/TPA/HQ |
| A | 16.20 | 9.87(2%) | 4.98 | 1.53(5%) | 60/15/20/5 |
| B | 16.20 | 8.23(2%) | 4.98 | 2.30(5%) | 60/12.5/20/7.5 |
| C | 16.20 | 6.58(2%) | 4.98 | 3.06(5%) | 60/10/20/10 |

Polymerization Temperatures

| Run | Atmospheric Pressure | | Vacuum |
|---|---|---|---|
| A | 286-330° C./26 min | + | 330-333° C./5 min |
| B | 284-350° C./25 min | + | 350° C./4 min |
| C | 284-332° C./25 min | + | 332-336° C./6 min |

Polymer Characterizations

| Run | Inherent Viscosity | Stick Temp. (°C.) |
|---|---|---|
| A | 0.97 | 208 |
| B | 1.12 | 240 |
| C | 0.88 | 250 |

Filament Extrusion

| Run | Melt Temp. (°C.) Cell (Spinneret) | Winding Speed (m/min) | No. of Holes |
|---|---|---|---|
| A | 310 (320) | 549 | 1 |
| B | 363 (364) | 549 | 1 |
| C | 360 (360) | 549 | 1 |

Heat Treatment

| Run | Cycle |
|---|---|
| A | RT-200° C./2 hr + 200-304° C./7 hr + 304° C./7 hr |
| B | RT-200° C./2 hr + 200-304° C./7 hr + 304° C./7 hr |
| C | RT-200° C./2 hr + 200-304° C./7 hr + 304° C./7 hr |

Tensile Properties

| Run | As-spun tex/T/E/M | Heat-Treated T/E/M | Maximum T |
|---|---|---|---|
| A | 0.76/2.6/0.9/281 | 9.1/3.9/236 | 11.5 |
| B | 0.77/2.4/0.7/335 | 12.1/4.5/280 | 14.2 |
| C | 0.69/2.3/0.5/414 | 9.1/3.1/303 | 10.0 |

Runs A and B produced excellent lustrous filaments. Processability for Run C was marginal in that the filament was quite dull, brittle, and of variable tex along its length.

I claim:

1. Fiber-forming copolyesters consisting essentially of units I, II and III having the structural formulas:

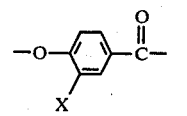 I

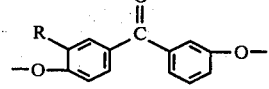 II

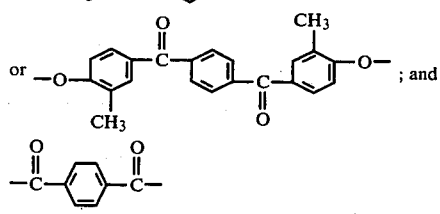 ; and

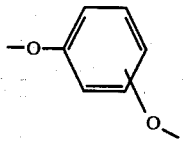 III where X and R are independently hydrogen, methyl- or chloro-, in the proportions of about 50-75 mol % of Unit I, about 10-25 mol % of Unit II, and about 10-25 mole % of Unit III with from 0-10 mol % of

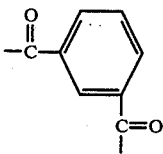

units selected from 1,3- or 1,4-dioxybenzene or from 0 to 5 mole % of

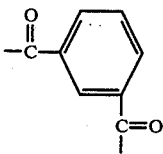

units.

2. A filament of a copolyester of claim 1.
3. A fiber-forming copolyester according to claim 1 wherein Unit I is present in an amount of about 60%.
4. A fiber-forming copolyester according to claim 1 wherein Unit I is p-oxybenzoyl and unit II is 3,4'-dioxybenzophenone.
5. A filament of the copolyester of claim 4.
6. A fiber-forming copolyester according to claim 1 wherein unit I is p-oxybenzoyl and unit II is 3'-methyl or 3'-chloro-3,4'-dioxybenzophenone.
7. A filament of the copolyester according to claim 6.
8. A fiber-forming copolyester according to claim 1 wherein unit I is 3-methyl or 3-chloro-p-oxybenzoyl and unit II is 3,4'-dioxybenzophenone.
9. A filament of the copolyester of claim 8.
10. A fiber-forming copolyester according to claim 1 wherein unit I is p-oxybenzoyl and unit II is 3,4'-dioxydiphenylether.
11. A filament of the copolyester of claim 10.

12. A fiber-forming copolyester according to claim 1 wherein unit I is p-oxybenzoyl and unit II is terephthaloyldi (3-methyl-4-oxybenzene).

13. A fiber-forming copolyester according to claim 12 which additionally contains 1,3-dioxyphenylene units.

14. A filament of the copolyester of claim 12.

15. A filament of the copolyester of claim 13.

16. Fiber-forming copolyesters consisting essentially of units I, II and III having the structural formulas:

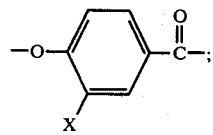

I

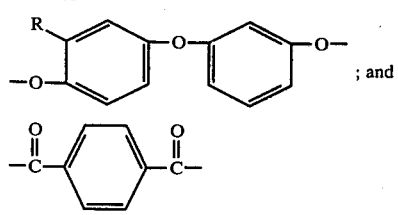

; and

II

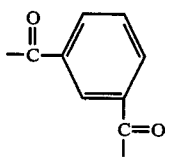

III wherein X and R are independently hydrogen, methyl- or chloro-, in the proportions of about 50–75 mol % of Unit I, about 10–25 mol % of Unit II, and about 10–25 mol % of Unit III with from 0–10 mol % of

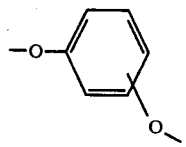

units selected from 1,3- or 1,4-dioxybenzene or from 0 to 5 mol % of units.

* * * * *